United States Patent [19]

Kamigata et al.

[11] Patent Number: 5,118,879
[45] Date of Patent: Jun. 2, 1992

[54] FLUOROALKYL DERIVATIVE AND PROCESS FOR PREPARING THE SAME

[75] Inventors: Nobumasa Kamigata, Kashiwa; Masato Yoshida, Tokyo; Hideo Sawada, Tsukuba; Masaharu Nakayama, Tsuchiura, all of Japan

[73] Assignee: Nippon Oil and Fats Co., Ltd., Tokyo, Japan

[21] Appl. No.: 601,736

[22] PCT Filed: Feb. 27, 1990

[86] PCT No.: PCT/JP90/00242

§ 371 Date: Oct. 25, 1990

§ 102(e) Date: Oct. 25, 1990

[87] PCT Pub. No.: WO90/09972

PCT Pub. Date: Sep. 7, 1990

[30] Foreign Application Priority Data

Feb. 27, 1989 [JP] Japan .................. 1-43147

[51] Int. Cl.$^5$ .............. C07C 17/04; C07C 22/08; C07C 205/06
[52] U.S. Cl. .................... 568/936; 570/127; 570/144; 568/927
[58] Field of Search ............ 570/127, 144; 568/936, 568/927

[56] References Cited

U.S. PATENT DOCUMENTS 3,326,928 6/1967 Mattson ........................... 570/144

FOREIGN PATENT DOCUMENTS 58-57324 4/1983 Japan .
2-200646A 8/1990 Japan .

OTHER PUBLICATIONS

Umemoto et al., Tetrahedron Letters, vol. 23, No. 11, pp. 1169-1172, 1982.
Kamigata et al. Phosphorus Sulfur, 19(2), 199-203, 1984; CA 101:72368c.
Dmowski, J. Fluorine Chem., 29(3), 287-96, 1985. CA105:97073y.
Minnesota Mining & Manufg. Co., CA 55:16452c, 1961.
Fuchikami et al., Tetrahedron Letters, 25(3), 303-6, 1986. CA100:209096.
Thaoi et al., J. Fluorine Chem., 6(4), 311-29, 1975. CA83:177764s.
Umemoto et al., Tetrahedron Letters, vol. 23, No. 35, PP3579-82, 1982.

Primary Examiner—Robert L. Stoll
Assistant Examiner—C. Sayala
Attorney, Agent, or Firm—Darby & Darby

[57] ABSTRACT

Fluoroalkyl derivatives which are novel compounds represented by the following general formula (I) or (II) of:

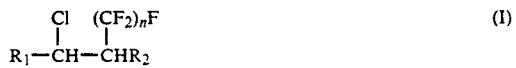

or

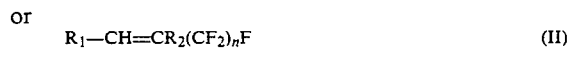

(wherein $R_1$ stands for

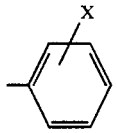

(where X stands for a hydrogen atom, a chlorine atom, a bromine atom, a fluorine atom, an iodine atom, a methyl group, an ethyl group, a methoxy group, an ethoxy group or a nitro group), an aroyloxy group, or an alkyl or alkoxycarbonyl group having 1 to 20 carbon atoms, and $R_2$ stands for a hydrogen atom or a methyl group; and n stands for an integer of from 1 to 20.) A process for the preparation of the derivative is a process comprising reacting an olefin compound and a fluoroalkanesulfonyl chloride in the presence of a metal catalyst, or a process comprising an additional alkali treatment step which follows the aforementioned process.

7 Claims, No Drawings

FLUOROALKYL DERIVATIVE AND PROCESS FOR PREPARING THE SAME

TECHNICAL FIELD

The present invention relates to a novel fluoroalkyl derivative and a process for preparing the same.

BACKGROUND TECHNOLOGY

Compounds in which fluoroalkyl groups are introduced into organic compounds attract public attention in recent years as they have physiological activities or like functions. Particularly, the compounds having the thus introduced fluoroalkyl groups have been known as intermediates for the synthesis of medicinal and agricultural chemicals and water- and oil-repellent agents.

However, fluoroalkyl derivatives represented by the following general formulae (IV) and (V) of:

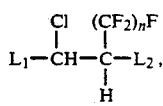  (IV)

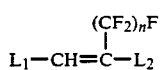  (V)

(In the formulae, $L_1$ stands for an aryl or alkyl group, $L_2$ stands for a hydrogen atom or a methyl group. And n stands for an integer of from 1 to 20.), i.e. fluoroalkyl group-containing chlorinated compounds, fluoroalkyl group-containing unsaturated compounds derived therefrom and the process for preparing the same, have not yet been known up to date.

An object of this invention is to provide fluoroalkyl derivatives which are utilizable as the intermediates for the synthesis of medicinal and agricultural chemicals and water- and oil-repellents, and to provide a process for preparing the same.

Another object of this invention is to provide a process for preparing a fluoroalkyl derivative easily at high yield without using any special device.

DISCLOSURE OF THE INVENTION

According to the present invention, there is provided a fluoroalkyl derivative represented by the following general formula (I) of

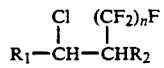  (I)

(In the formula, $R_1$ stands for

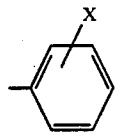

(where X stands for a hydrogen atom, a chlorine atom, a bromine atom, a fluorine atom, an iodine atom, a methyl group, an ethyl group, a methoxy group, an ethoxy group or a nitro group), an aroyloxy group, or an alkyl or alkoxycarbonyl group having 1 to 20 carbon atoms, and $R_2$ stands for a hydrogen atom or a methyl group. Meantime, n stands for an integer of from 1 to 20.)

Also provided by the present invention is a fluoroalkyl derivative represented by the following general formula (II) of

  (II)

(In the formula, $R_1$ and $R_2$ are the same as $R_1$ and $R_2$ in the preceding general formula (I).)

Further provided by the present invention is a process for preparing a fluoroalkyl derivative represented by the aforementioned general formula (I) or fluoroalkyl derivatives represented by the aforementioned general formulae (I) and (II), comprising reacting an olefin compound represented by the following general formula (III) of:

$$R_1-CH=CH-R_2 \quad (III)$$

(wherein $R_1$ and $R_2$ are the same as $R_1$ and $R_2$ in the preceding general formula (I).)
with a fluoroalkanesulfonyl chloride represented by the general formula (IV) of:

$$F(CF_2)_nSO_2Cl \quad (IV)$$

(wherein n stands for an integer of from 1 to 20) in the presence of a metal catalyst.

Further provided by the present invention is a process for preparing a fluoroalkyl derivative represented by the aforementioned general formula (II), comprising reacting an olefin compound represented by the aforementioned general formula (III) with a fluoroalkanesulfonyl chloride represented by the general formula (IV) in the presence of a metal catalyst to obtain a compound represented by the general formula (I), and then treating the compound (I) with an alkali.

BEST EMBODIMENTS FOR THE PRACTICE OF THE INVENTION

The present invention will be described more in detail hereinbelow.

The fluoroalkyl derivatives of the invention may be represented by the following general formulae (I) and (II) of:

  (I)

  (II)

(In the formulae, $R_1$ stands for

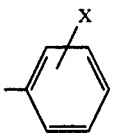

(where X stands for a hydrogen atom, a chlorine atom, a bromine atom, a fluorine atom, an iodine atom, a methyl group, an ethyl group, a methoxy group, an ethoxy group or a nitro group), an aroyloxy group, or an alkyl or alkoxycarbonyl group having 1 to 20 carbon group. Meantime, n stands for an integer of from 1 to 20.) It is difficult to prepare those each including $R_1$ which is an alkyl group having not less than 21 carbon atoms.

Preferable examples of the fluoroalkyl derivatives represented by the aforementioned general formula (I) include: 1-phenyl-1-chloro-3,3,3-trifluoropropane, 1-phenyl-1-chloro-2-methyl-3,3,3-trifluoropropane, 1-p-chlorophenyl-1-chloro-3,3,3-trifluoropropane, 1-p-tolyl-1-chloro-2-methyl-3,3,3-trifluoropropane, 1-m-nitrophenyl-1-chloro-3,3,3-trifluoropropane, 3-chloro-1,1,1-trifluorononane, 3-chloro-1,1,1-trifluoroundecane, 3-chloro-1,1,1-trifluorotridecane, 1-chloro-2-perfluorobutyl-1-phenylethane, 1-chloro-2-perfluorohexyl-1-phenylethane, 1-chloro-1-phenyl-2-perfluorobutyl-propane, 1-chloro-1-phenyl-2-perfluorohexyl-propane, 1-chloro-1-p-chlorophenyl-2-perfluorobutyl-ethane, 1-chloro-1-p-chlorophenyl-2-perfluorohexyl-ethane, 1-chloro-1-p-tolyl-2-perfluorobutyl-ethane, 1-chloro-1-p-tolyl-2-perfluorohexyl-ethane, 1-chloro-1-m-nitrophenyl-2-perfluorobutyl-ethane, 1-chloro-1-m-nitrophenyl-2-perfluorohexyl-ethane, 1-chloro-1-hexyl-2-perfluorobutyl-ethane, 1-chloro-1-hexyl-2-perfluorohexyl-ethane, 1-chloro-1-octyl-2-perfluorohexyl-ethane, 1-chloro-1-octyl-2-perfluorobutyl-ethane, 1-chloro-1-decyl-2-perfluorobutyl-ethane, 1-chloro-1-decyl-2-perfluorohexyl-ethane, etc.

Preferable examples of the fluoroalkyl derivatives represented by the aforementioned general formula (II) include: 1-phenyl-2-trifluoromethylpropene, 1-phenyl-3,3,3-trifluoropropene, 1-p-chlorophenyl-3,3,3-trifluoropropene, 1-phenyl-2-perfluorobutylpropene, 1-phenyl-2-perfluorohexylpropene, 1-phenyl-2-perfluorobutylethene, 1-p-chlorophenyl-2-perfluorobutylethene, 1-p-chlorophenyl-2-perfluorohexylethene, 1-p-tolyl-2-perfluorobutylethene, 1-p-tolyl-2-perfluorohexylethene, 1-m-nitrophenyl-2-perfluorobutylethene, 1-m-nitrophenyl-2-perfluorohexylethene, 1-hexyl-2-perfluorobutylethene, 1-hexyl-2-perfluorohexylethene, 1-octyl-2-perfluorobutylethene, 1-octyl-2-perfluorohexylethene, 1-decyl-2-perfluorobutylethene, 1-decyl-2-perfluorohexylethene, 1-p-tolyl-3,3,3-trifluoropropene, 1-m-nitrophenyl-3,3,3-trifluoropropene, 1-hexyl-3,3,3-trifluoropropene, 1-octyl-3,3,3-trifluoropropene, 1-decyl-3,3,3-trifluoropropene, etc.

According to the present invention, by a first process for preparing the fluoroalkyl derivative represented by the aforementioned general formula (I) or the fluoroalkyl derivatives represented by the general formulae (I) and (II), the derivative may be prepared by the process which comprises reacting a specific olefin compound with a specific fluoroalkanesulfonyl chloride in the presence of a metal catalyst; whereas by a second process for preparing the fluoroalkyl derivative represented by the aforementioned general formula (II), the derivative may be prepared by the process which comprises producing a fluoroalkyl derivative represented by the general formula (I) in the presence of the metal catalyst and then treating the derivative with an alkali.

The specific olefin compounds which are used in the first and second preparation processes of this invention may be represented by the following general formula (III) of:

$$R_1-CH=CH-R_2 \qquad (III)$$

In the formula, $R_1$ and $R_2$ are the same as defined in the preceding general formula (I). Preferable examples of the olefin compound represented by the general formula (III) set forth above includes styrene, β-methylstyrene, p-chlorostyrene, p-methylstyrene, m-nitrostyrene, 1-octene, 1-decene, 1-dodecene, etc. Further, the aforementioned specific fluoroalkanesulfonyl chloride used in the process of this invention may be represented by the following general formula (IV) of:

$$F(CF_2)_nSO_2Cl \qquad (IV)$$

In the formula, n stands for an integer of from 1 to 20. Preparation of a fluoroalkanesulfonyl chloride where n is not less than 21 is difficult. $F(CF_2)_n$ in the general formula (IV) set forth above is $CF_3$, $F(CF_2)_2$, $F(CF_2)_3$, $F(CF_2)_4$, $F(CF_2)_5$, $F(CF_2)_6$, $F(CF_2)_7$, $F(CF_2)_8$, $F(CF_2)_9$, $F(CF_2)_{10}$, $F(CF_2)_{11}$, $F(CF_2)_{12}$, $F(CF_2)_{13}$, $F(CF_2)_{14}$, $F(CF_2)_{15}$, $F(CF_2)_{16}$, $F(CF_2)_{17}$, $F(CF_2)_{18}$, $F(CF_2)_{19}$, and $F(CF_2)_{20}$.

Preferable metal catalysts used in the first and second processes of this invention include, for example, cuprous oxide, cupric cyanide, copper sulfate, cupric acetate, copper sulfide, cupric chloride, cuprous chloride, cuprous bromide, cupric bromide, copper iodide, ferrous chloride, ferric chloride, pentacarbonyl iron, iron sulfate, hexacarbonyl molybdenum, hexacarbonyl chromium, chromium chloride, dichlorotris(triphenylphosphine) ruthenium, dichlorotetrakis(triphenylphosphine) ruthenium, chlorotris(triphenylphosphine) rhodium, pentacarbonyl ruthenium, dodecacarbonyl ruthenium-(III), tricarbonyl-($\eta^4$-cyclooctatetraene) ruthenium, dicarbonylbis($\eta$-allyl) ruthenium, bromocarbonyl($\eta$-allyl) ruthenium, tetrachlorohexacarbonyl ruthenium, dichlorotricarbonyl ruthenium, tetracarbonylbis($\eta$-cyclopentadienyl) ruthenium, diiododicarbonyl ruthenium, bis($\eta$-cyclopentadienyl) ruthenium, ($\eta$-cyclopentadienyl)($\eta$-acetylcyclopentadienyl) ruthenium, ($\eta$-cyclopentadienyl)($\eta$-methylcyclopentadienyl) ruthenium, chlorohydridotris(triphenylphosphine) ruthenium, dihydrido(dinitrogen)tris(triphenylphosphine) ruthenium(II), tetrahydridotris(triphenylphosphine) ruthenium, hydridotetrakis(triphenylphosphine) ruthenium, tetracarbonylbis(cyclopentadienyl) ruthenium, iododicarbonyl($\eta$-cyclopentadienyl) ruthenium, dicarbonyl(methyl)($\eta$-cyclopentadienyl) ruthenium, chlorodicarbonyl($\eta$-cyclopentadienyl) ruthenium, tetracarbonylbis(cyclopentadienyl) ruthenium, ruthenium chloride, trans-[chlorohydridobis(1,2-bisdiethylphosphinoethane)] ruthenium(II), ($\eta^4$-cyclohexadiene) ($\eta$-benzene) ruthenium, dichloro(1,5-cyclooctanediene) ruthenium, etc.

Examples of alkalies used for the alkali treatment in the second process of this invention include potassium hydroxide, sodium hydroxide, potassium carbonate, pyridine, triethylamine, tributylamine, etc.

In the first and second processes of this invention, the molar ratio to be charged among the aforementioned olefin compound, the fluoroalkanesulfonyl chloride represented by the general formula (IV), and the metal catalyst ranges preferably from 1:0.1–1:0.001–0.50, particularly preferably from 1:0.5–1:0.005–0.50. It is not preferred that the molar ratio between the fluoroalkanesulfonyl chloride and the metal catalyst be less than 0.1 and 0.001, since the yield of the produced fluoroalkyl derivative is decreased; whereas it is not preferred that the ratio exceeds 1 and 0.50, since unreacted materials are left after the completion of the reaction to make it difficult to isolate the objective product, leading to disadvantages from the industrial standpoint of view.

In the first and second processes of this invention, it is desirous that the olefin compound represented by the aforementioned general formula (III) be reacted with the fluoroalkanesulfonyl chloride represented by the general formula (IV) in the presence of the metal catalyst at a reaction temperature of from 0° to 200° C., particularly preferably within the range of from 20° to 150° C. It is not preferred that the reaction temperature be lower than 0° C. since the time required for the reaction is prolonged, and in contrary, it is not preferred that the temperature be above 200° C. since the pressure during the reaction step is raised to bring difficulty in reaction operation. As to the reaction time, the reaction may be completed generally over a period of from 30 minutes to 50 hours, and it is practically preferred that the conditions for the reaction be determined so that the reaction time ranges within an hour to 24 hours.

In the second process of this invention, in order to prepare the fluoroalkyl derivative represented by the aforementioned general formula (I) by the reaction carried out in the presence of the metal catalyst followed by the treatment with an alkali, the fluoroalkyl derivative represented by the aforementioned general formula (II) may be prepared through the reaction in the presence of the aforementioned metal catalyst followed by addition of an alkali to be treated therewith, or the prepared fluoroalkyl derivative may be isolated and then treated with an alkali. The reaction temperature and the reaction time for the treatment with an alkali as described above may be set to similar reaction conditions as for the reaction carried out in the presence of the metal catalyst. In this step, it is preferred that the molar ratio between the charged alkali and fluoroalkyl derivative ranges within 1:0.001–3, particularly preferably within 1:0.05–2. It is disadvantageous, from the industrial standpoint of view, to set the molar ratio of the fluoroalkyl derivative in an amount of less than 0.01 since the reaction temperature is raised, whereas it is not preferred to set the molar ratio thereof in an amount of more than 3 since the yield of the compound represented by the general formula (II) is decreased.

The reaction products obtained by the first and second processes of this invention may be purified through the known methods, such as column chromatography.

As will be appreciated from the foregoing, the fluoroalkyl derivatives of this invention are novel compounds which may be used as medicinal and agricultural chemicals, or intermediates for the synthesis thereof, and also as water- and oil-repellents. The processes of this invention have industrial utility since the fluoroalkyl derivatives can be prepared easily at high yield simply by reacting the compounds in the presence of the metal catalyst, or optionally by treating with alkali, without using any special device.

EXAMPLES

In the following description, the present invention will be described more in detail with reference to Examples and Comparative Examples, but the invention should not be limited thereto.

EXAMPLE 1

To 4 ml of benzene added were 2 mmol (0.208 g) of styrene, 2 mmol (0.337 g) of trifluoromethanesulfonyl chloride and 0.02 mmol (0.019 g) of dichlorotris(triphenylphosphine) ruthenium, followed by purging and sealing. Then, the reaction was allowed to proceed at 120° C. for 24 hours, the metal catalyst was removed by column chromatography, and the product was purified by gel permeation chromatography. As the result, obtained was 1-phenyl-1-chloro-3,3,3-trifluoropropane at a yield of 76%. The following are the results of IR, $^1$H-NMR, MS and Exact MS analyses.

| °IR(Neat) cm$^{-1}$ | 3030, 1380, 1270, 1140 |
|---|---|
| °$^1$H-NMR(CDCl$_3$)δ | 2.50 to 3.28(2H, m), |
| | 5.40(1H, t, J=7.2 Hz), |
| | 7.26(5H, S) |
| °MS, m/z | 208(M$^+$), 173, 127, 125, 109, 105, 104, 103 |
| °Exact MS, m/z | 208.0267 |
| | Cald. C$_9$H$_8$ClF$_3$: m/z 208.0267 |

EXAMPLE 2

Reaction was carried out generally in accordance with Example 1, except that styrene was replaced by p-chlorostyrene, whereby 1-p-chlorophenyl-1-chloro-3,3,3-trifluoropropane was obtained at a yield of 69%. The results of analyses of the product are set forth below.

| °IR(Neat) cm$^{-1}$ | 1900, 1600, 1490, 1380, 1260, 1140 |
|---|---|
| °$^1$H-NMR(CDCl$_3$)δ | 2.46 to 3.21(2H, m) |
| | 4.98(1H, t, J=7.2 Hz), |
| | 7.18(4H, S) |
| °MASS, m/z | 244, 242(M$^+$), 209, 207, 161, 159 145, 143 |
| °Exact MS, m/z | 241.9879 |
| | Cald. C$_9$H$_7$Cl$_2$F$_3$: m/z 241.9877 |

EXAMPLE 3

Reaction was carried out generally in accordance with Example 1, except that styrene was replaced by p-methylstyrene, whereby 1-p-methylphenyl-1-chloro-3,3,3-trifluoropropane was obtained at a yield of 55%. The results of analyses of the product are set forth below.

| °IR(Neat) cm$^{-1}$ | 3020, 2920, 1610, 1510, 1420, 1380, 1260, 1140 |
|---|---|
| °$^1$H-NMR(CDCl$_3$)δ | 2.30(3H, S), 2.50 to 3.23(2H, m), |
| | 5.01(1H, t, J=6.6 Hz), |
| | 7.11(4H, S) |
| °MASS, m/z | 222(M$^+$), 187, 147, 139, 123, 117, 115 |
| °Exact MASS, m/z | 222.0430 |
| | Cald. C$_{10}$H$_{10}$ClF$_3$: m/z 222.0423 |

EXAMPLE 4

Reaction was carried out generally in accordance with Example 1, except that styrene was replaced by m-nitrostyrene, whereby 1-m-nitrophenyl-1-chloro-3,3,3-trifluoropropane was obtained at a yield of 58%. The results of analyses of the product are set forth below.

| °IR(Neat) cm$^{-1}$ | 3070, 1530, 1350, 1250, 1140 |
|---|---|
| °$^1$H-NMR(CDCl$_3$)δ | 2.60 to 3.22(2H, m), |
| | 5.13(1H, t, J=6.6 Hz), |
| | 7.14 to 8.31(4H, m) |
| °MASS, m/z | 253(M$^+$), 218, 170, 154, 151, 143, 103, 77 |
| °Exact MASS, m/z | 253.0087 |

-continued

Cald. C₉H₇ClF₃NO₂: m/z 253.0117

EXAMPLE 5

Reaction was carried out generally in accordance with Example 1, except that styrene was replaced by 1-octene, whereby 3-chloro-1,1,1-trifluorononane was obtained at a yield of 73%. The results of analyses of the product are set forth below.

| | |
|---|---|
| °IR(Neat) cm⁻¹ | 2930, 1460, 1380, 1260, 1150 |
| °¹H-NMR(CDCl₃)δ | 0.60 to 2.04(13H, m), 2.39, 2.68(2H, ABq, J=10.2 Hz, 6.6 Hz), 4.06(1H, quintet) |
| °¹³C-NMR(CDCl₃) | 14.0, 22.6, 26.0, 28.7, 31.7, 38.2, 42.6(q, $J_{CCF}$=28.1 Hz), 54.3(q, $J_{CCF}$=3.7 Hz) |

EXAMPLE 6

Reaction was carried out generally in accordance with Example 1, except that dichlorotris(triphenylphosphine) ruthenium and benzene were replaced by cuprous chloride and acetonitrile, respectively, whereby 1-phenyl-1-chloro-3,3,3-trifluoropropane was obtained at a yield of 65%. The results of analyses of the product were the same as described in Example 1.

EXAMPLE 7

Reaction was carried out generally in accordance with Example 1, except that dichlorotris(triphenylphosphine) ruthenium and benzene were replaced, respectively, by iron sulfate and acetonitrile, whereby 1-phenyl-1-chloro-3,3,3-trifluoropropane was obtained at a yield of 61%. The results of analyses of the product were the same as described in Example 1.

EXAMPLE 8

Reaction was carried out generally in accordance with Example 1, except that styrene was replaced by β-methylstyrene, whereby 1-phenyl-1-chloro-2-fluoroalkylpropane was obtained at a yield of 71%. The results of analyses of the product are set forth below.

| | |
|---|---|
| °IR(Neat) cm⁻¹ | 3000, 1450, 1360, 1260, 1170, 1130 |
| °¹H-NMR(CDCl₃)δ | [1.09(d, J=7.2 Hz) + 1.26(d, J=7.2 Hz); 3H], 2.27 to 3.17(1H, m), [5.06 (d, J=6.6 Hz + 5.22(d, J=4.2 Hz); 1H], 7.03 to 7.47(5H, m) |
| °MASS, m/z | 222(M⁺), 187, 127, 125, 109, 91 |
| °Exact MASS, m/z | 222.0409 Cald. C₁₀H₁₀ClF₃: m/z: 222.0423 |

EXAMPLE 9

To 7 ml of ethanol added was 0.6 mmol (0.126 g) of 1-phenyl-1-chloro-2-trifluoromethylpropane, and then 2 mmol (0.112 g) of potassium hydroxide was added thereto and allowed to react at 50° C. for 18 hours, whereby 1-phenyl-2-trifluoromethylpropene was obtained at a yield of 71%. The results of analyses of the product are shown below.

| | |
|---|---|
| °IR(Neat) cm⁻¹ | 1490, 1440, 1360, 1320, 1290, 1160, 1110 |
| °¹H-NMR(CDCl₃)δ | 1.84 to 2.17(3H, m), 6.63 to 7.08(1H, m), 7.10 to 7.46(5H, m) |
| °MASS, m/z | 186(M⁺), 165, 117, 115, 91 |
| °Exact MASS, m/z | 186.0680 Cald. C₁₀H₉F₃, m/z: 186.0656 |

EXAMPLE 10

Reaction was carried out generally in accordance with Example 1, except that styrene was replaced by 1-decene, whereby 3-chloro-1,1,1-trifluoroundecane was obtained at a yield of 79%. The results of analyses of the product are set forth below.

| | |
|---|---|
| °IR(Neat) cm⁻¹ | 2920, 1460, 1380, 1260, 1240, 1145 |
| °¹H-NMR(CDCl₃)δ | 0.60 to 2.07(17H, m), 2.38 to 2.68 (2H, ABq, J=10.2 Hz, 6.6 Hz), 4.05(1H, quintet, J=6.0 Hz) |
| °¹³C-NMR(CDCl₃)δ | 14.1, 22.8, 26.0, 29.0, 29.3, 29.5, 31.9, 38.2, 42.6 (q, $J_{CCF}$=28.2 Hz) 54.2 (q, $J_{CCCF}$=3.7 Hz) |
| °MASS, m/z | 244(M⁺), 175, 151, 137, 123, 98, 85 |
| °Exact MASS, m/z | 244.1306 Cald. C₁₀H₂₀ClF₃: m/z: 244.1206 |

EXAMPLE 11

Reaction was carried out generally in accordance with Example 1, except that styrene was replaced by 1-dodecene, whereby 3-chloro-1,1,1-trifluorotridecane was obtained at a yield of 76%. The results of analyses of the product are set forth below.

| | |
|---|---|
| °IR(Neat) cm⁻¹ | 2930, 1460, 1380, 1260, 1240, 1150 |
| °¹H-NMR(CDCl₃)δ | 0.60 to 2.00(21H, m), 2.39 to 2.67 (2H, ABq, J=10.2 Hz, 6.0 Hz) 4.05(1H, quintet, J=6.0 Hz) |
| °MASS, m/z | 272(M⁺), 187, 173, 165, 151, 137, 123, 97, 85 |
| °Exact MASS, m/z | 272.1525 Cald. C₁₃H₂₄ClF₃: m/z: 272.1519 |

EXAMPLE 12

Reaction was carried out generally in accordance with Example 1, except that trifluoromethanesulfonyl chloride was replaced by perfluorohexanesulfonyl chloride, whereby 1-phenyl-1-chloro-2-perfluorohexylethane and 1-phenyl-2-perfluorohexylethene were obtained, respectively, at a yield of 42% and 38%. The results of analyses of the products are set forth below.

| | |
|---|---|
| °1-Phenyl-1-chloro-2-perfluorohexylethane | |
| °IR(Neat) cm⁻¹ | 1360 |
| °¹H-NMR(CDCl₃)δ | 2.53 to 3.37(2H, m), 5.20(1H, t, J=7.0 Hz), 7.33(5H, s) |
| °¹³C-NMR(CDCl₃)δ | 41.0(t, $J_{CCF}$=20.8 Hz), 54.1, 126.9, 129.3, 140.4 |
| °MASS, m/z | 458(M⁺), 423 |
| °Exact MASS, m/z | 458.0135 Cald. C₁₄H₈ClF₁₃: m/z: 458.0107 |
| °1-Phenyl-2-perfluorohexylethene | |
| °IR(Neat) cm⁻¹ | 1660, 1585, 1500, 1450, 1365 |
| °¹H-NMR(CDCl₃)δ | 5.73 to 6.55(1H, m), 7.09(1H, d, J=10.2 Hz), 7.33(5H, s) |
| °¹³C-NMR(CDCl₃) | 114.6(t, $J_{CCF}$=23.2 Hz), 127.7, 129.0, 130.2, 133.8, 139.9(t, $J_{CCCF}$=9.8 Hz) |
| °MASS, m/z | 422(M⁺), 403, 353, 153, 133, 69 |

*Exact MASS,m/z  422.0292
                 Cald. $C_{14}H_7ClF_{13}$: m/z 422.0340

EXAMPLE 13

Reaction was carried out generally in accordance with Example 1, except that styrene was replaced by p-methylstyrene and trifluoromethanesulfonyl chloride was replaced by perfluorohexanesulfonyl chloride, whereby 1-p-tolyl-1-chloro-2-perfluorohexylethane and 1-p-tolyl-2-perfluorohexylethene were obtained, respectively, at a yield of 61% and 28%. The results of analyses of the products are set forth below.

```
*1-p-Tolyl-1-chloro-2-perfluorohexylethane
*IR(Neat) cm⁻¹        3030, 2930, 1615, 1515, 1440, 1365
*¹H-NMR(CDCl₃)δ       2.35(3H, s), 2.51 to 3.37(2H, m),
                      5.20(1H, t, J=6.9 Hz), 7.16,
                      7.27(4H, ABq, J=8.1 Hz)
*¹³C-NMR(CDCl₃)δ      21.1, 40.8(t, J_CCF=22.0 Hz), 54.0,
                      126.7, 129.7, 137.4, 139.1
*MASS, m/z            472(M⁺), 437, 167, 139, 123, 69
*Exact MASS,m/z       472.0263
                      Cald. C₁₅H₁₀ClF₁₃: m/z: 472.0263
*1-p-Tolyl-2-perfluorohexylethene
*IR(Neat) cm⁻¹        3030, 2930, 1655, 1610, 1515, 1415,
                      1365
*¹H-NMR(CDCl₃)δ       2.37(3H, s), 5.72 to 6.53(1H, m),
                      6.94 to 7.05(1H, m), 7.18,
                      7.34(4H, ABq, J=8.1 Hz)
*¹³C-NMR(CDCl₃)δ      21.3, 113.4(t, J_CCF=22.0 Hz),
                      127.7, 129.7, 131.0,
                      139.8(t, J_CCCF=9.2 Hz), 140.6
*Exact MASS,m/z       436.0521
                      Cald. C₁₅H₉F₁₃: m/z: 436.0496
```

EXAMPLE 14

Reaction was carried out generally in accordance with Example 1, except that styrene was replaced by p-chlorostyrene and trifluoromethanesulfonyl chloride was replaced by perfluorohexanesulfonyl chloride, whereby 1-p-chlorophenyl-1-chloro-2-perfluorohexylethane and 1-p-chlorophenyl-2-perfluorohexylethene were obtained, respectively, at a yield of 41% and 20%. The results of analyses of the products are set forth below.

```
*1-p-Chlorophenyl-1-chloro-2-perfluorohexylethane
*IR(Neat) cm⁻¹        1600, 1490, 1420, 1365
*¹H-NMR(CDCl₃)δ       2.50 to 3.33(2H, m),
                      5.19(1H, t, J=6.9 Hz),
                      7.33(4H, s)
*¹³C-NMR(CDCl₃)δ      41.0(t, J_CCF=20.8 Hz),
                      53.3(t, J_CCF=3.1 Hz),
                      128.3, 129.4, 135.3, 138.9
*Exact MASS,m/z       491.9745
                      Cald. C₁₄H₇Cl₂F₁₃: m/z: 491.9717
*1-p-Chlorophenyl-2-perfluorohexylethene
*IR(Neat) cm⁻¹        1660, 1600, 1500, 1415, 1365
*¹H-NMR(CDCl₃)δ       5.77 to 6.60(1H, m),
                      7.15(1H, d, J=14.4 Hz),
                      7.40(4H, s)
*¹³C-NMR(CDCl₃)δ      115.2(t, J_CCF=23.2 Hz), 128.9,
                      129.3, 132.1, 136.3,
                      138.6(t, J_CCCF=3.1 Hz)
*Exact MASS,m/z       455.9954
                      Cald. C₁₄H₆ClF₁₃: m/z: 455.9950
```

EXAMPLES 15 TO 17

Reactions were carried out generally in accordance with Example 1, except that trifluoromethanesulfonyl chloride was replaced by perfluorohexanesulfonyl chloride and styrene was replaced, respcetively, by 1-hexene (Example 15), 1-heptene (Example 16) and 1-octene (Example 17), whereby 1-butyl-1-chloro-2-perfluorohexylethane (Example 15), 1-heptyl-1-chloro-2-perfluorohexylethane (Example 16) and 1-hexyl-1-chloro-2-perfluorohexylethane (Example 17) were obtained, respectively, at a yield of 63%, 69% and 73%. The results of analyses of respective products are set forth below.

```
*1-Butyl-1-chloro-2-perfluorohexylethane
*IR(Neat) cm⁻¹        2960, 2930, 2870, 1470, 1440, 1360
*¹H-NMR(CDCl₃)δ       0.72 to 2.13(9H, m),
                      2.16 to 3.03(2H, m),
                      4.26(1H, quintet, J=6.2 Hz)
*¹³C-NMR(CDCl₃)δ      13.8, 22.2, 28.3, 38.7,
                      39.7(t, J_CCF=22.6 Hz), 53.5
*MASS, m/z            402(M⁺-HCl), 69
*Exact MASS,m/z       402.0641
                      Cald. C₁₂H₁₁F₁₃: m/z: 402.6053
*1-Heptyl-1-chloro-2-perfluorohexylethane
*IR(Neat) cm⁻¹        2960, 2930, 2860, 1465, 1435, 1360
*¹H-NMR(CDCl₃)δ       0.69 to 2.12(11H, m),
                      2.14 to 3.03(2H, m),
                      4.24(1H, quintet, J=6.0 Hz)
*¹³C-NMR(CDCl₃)δ      13.9, 22.6, 25.8, 31.3, 39.0,
                      39.7(t, J_CCF=18.9 Hz), 53.5
*MASS m/z             416 (M⁺-HCl), 387, 69
*Exact MASS,m/z       416.0809
                      Cald. C₁₃H₁₃F₁₃: m/z: 416.0848
*1-Hexyl-1-chloro-2-perfluorohexylethane
*IR(Neat) cm⁻¹        29.60, 2940, 2870, 1470, 1435, 1365
*¹H-NMR(CDCl₃)δ       0.67 to 2.09(13H, m),
                      2.13 to 3.01(2H, m),
                      4.24(1H, quintet, J=6.2 Hz)
*¹³C-NMR(CDCl₃)δ      14.0, 22.6, 26.1, 28.7, 31.7, 38.9
                      39.7(t, J_CCF=18.9 Hz), 53.5
*MASS, m/z            430(M⁺-HCl), 401, 387
*Exact MASS,m/z       430.0967
                      Cald. C₁₄H₁₅F₁₃: m/z 430.0967
```

We claim:

1. A fluoroalkyl derivative selected from the group consisting of
1-phenyl-1-chloro-2-methyl-3,3,3-trifluoropropane,
1-p-chlorophenyl-1-chloro-3,3,3-trifluoropropane,
1-p-tolyl-1chloro-2-methyl-3,3,3-trifluoropropane,
1-m-nitrophenyl-1-chloro-3,3,3-trifluoropropane,
3-chloro-1,1,1-trifluorononane, 3-chloro-1,1,1-trifluoroundecane,
3-chloro-1,1,1-trifluorotridecane,
1-chloro-2-perfluorobutyl-1-phenylethane,
1-chloro-2-perfluorohexyl-1-phenylethane,
1-chloro-1-phenyl-2-perfluorobutyl-propane,
1-chloro-1-phenyl-2-perfluorohexyl-propane,
1-chloro-1-p-chlorophenyl-2-perfluorobutyl-ethane,
1-chloro-1-p-chlorophenyl-2-perfluorohexyl-ethane,
1-chloro-1-p-tolyl-2-perfluorobutyl-ethane,
1-chloro-1-p-tolyl-2-perfluorohexyl-ethane,
1-chloro-1-m-nitrophenyl-2-perfluorobutyl-ethane,
1-chloro-1-m-nitrophenyl-2-perfluorohexyl-ethane,
1-chloro-1-hexyl-2-perfluorobutyl-ethane,
1-chloro-1-hexyl-2-perfluorohexyl-ethane,
1-chloro-1-octyl-2-perfluorohexyl-ethane,
1-chloro-1-octyl-2-perfluorobutyl-ethane,
1-chloro-1-decyl-2-perfluorobutyl-ethane and
1-chloro-1-decyl-2-perfluorohexyl-ethane.

2. A process for preparing a fluoroalkyl derivative represented by the general formula (I):

$$\underset{R_1-CH-CHR_2}{\overset{Cl\quad (CF_2)_nF}{|\quad\quad|}} \qquad (I)$$

wherein $R_1$ stands for an unsubstituted phenyl group; a monosubstituted phenyl group having a substituent selected from the group consisting of chlorine, bromine, fluorine, iodine, methyl, ethyl, methoxy, ethoxy, and nitro; and aroyloxy, alkyl or alkoxycarbonyl having 1 to 20 carbon atoms; and $R_2$ stands for hydrogen or methyl; and n stands for an integer from 1 to 20, said method comprising reacting, in the presence of a metal catalysts, an olefin compound represented by the following general formula (III):

$$R_1-CH=CH-R_2 \qquad (III)$$

wherein $R_1$, $R_2$, and n have the same meaning as in Formula I with a fluoroalkanesulfonyl chloride represented by the general formula (IV):

$$F(CF_2)_nSO_2Cl \qquad (IV)$$

wherein n stands for an integer of from 1 to 20.

3. The process for preparing a fluoroalkyl derivative as claimed in claim 2, wherein said olefin compound represented by said general formula (III) is selected from the group consisting of styrene, β-methylstyrene, p-chlorostyrene, p-methylstyrene, m-nitrostyrene, 1-octene, 1-decene and 1-dodecene.

4. The process for preparing a fluoroalkyl derivative as claimed in claim 2, wherein $F(CF_2)_n$- in the fluoroalkanesulfonyl chloride represented by said general formula (IV) is selected from the group consisting of $CF_3$, $F(CF_2)_2$, $F(CF_2)_3$, $F(CF_2)_4$, $F(CF_2)_5$, $F(CF_2)_6$, $F(CF_2)_7$, $F(CF_2)_8$, $F(CF_2)_9$, $F(CF_2)_{10}$, $F(CF_2)_{11}$, $F(CF_2)_{12}$, $F(CF_2)_{13}$, $F(CF_2)_{14}$, $F(CF_2)_{15}$, $F(CF_2)_{16}$, $F(CF_2)_{17}$, $F(CF_2)_{18}$, $F(CF_2)_{19}$ and $F(CF_2)_{20}$.

5. The process for preparing a fluoroalkyl derivative as claimed in claim 2, wherein said metal catalyst is selected from the group consisting of cuprous oxide, cupric cyanide, copper sulfate, cupric acetate, copper sulfide, cupric chloride, cuprous chloride, cuprous bromide, cupric bromide, copper iodide, ferrous chloride, ferric chloride, pentacarbonyl iron, iron sulfate, hexacarbonyl molybdenum, hexacarbonyl chromium, chromium chloride, dichlorotris(triphenylphosphine) ruthenium, dichlorotetrakis(triphenylphosphine) ruthenium, chlorotris(triphenylphosphine) rhodium, pentacarbonyl ruthenium, dodecacarbonyl ruthenium(III), tricarbonyl(β⁴-cyclooctatetraene) ruthenium, dicarbonylbis(η-allyl) ruthenium, bromocarbonyl(η-allyl) ruthenium, tetrachlorohexacarbonyl ruthenium, dichlorotricarbonyl ruthenium, tetracarbonylbis(η-cyclopentadienyl) ruthenium, diiododicarbonyl ruthenium, bis(η-cyclopentadienyl) ruthenium, (η-cyclopentadienyl)(η-acetylcyclopentadienyl) ruthenium, (η-cyclopentadienyl)(η-methylcyclopentadienyl) ruthenium, chlorohydridotris(triphenylphosphine) ruthenium, dihydride(dinitrogen)tris(triphenylphosphine) ruthenium(II), tetrahydridotris(triphenylphosphine) ruthenium, hydridotetrakis(triphenylphosphine) ruthenium, tetracarbonylbis(cyclopentadienyl) ruthenium, iododicarbonyl(η-cyclopentadienyl) ruthenium, dicarbonyl(methyl)(η-cyclopentadienyl) ruthenium, chlorodicarbonyl(η-cyclopentadienyl) ruthenium, tetracarbonylbis(cyclopentadienyl) ruthenium, ruthenium chloride, trans-[chlorohydoridobis(1,2-bisdiethylphosphinoethane)] ruthenium(II), (η-cyclohexadiene) (η-benzene) ruthenium, dichloro(1,5-cyclooctanediene) ruthenium and mixtures thereof.

6. The process for preparing a fluoroalkyl derivative as claimed in claim 2, wherein a molar ratio charged of said olefin compound, said fluoroalkanesulfonyl chloride and said metal catalyst ranges from 1:0.1-1:0.0-01-0.50.

7. The process for preparing a fluoroalkyl derivative as claimed in claim 2, wherein said reaction is carried out at 0° to 200° C.

* * * * *